United States Patent
Cornelius

[11] Patent Number: 6,080,117
[45] Date of Patent: Jun. 27, 2000

[54] GUIDE WIRE EXTENSION SYSTEM

[75] Inventor: Richard G. Cornelius, Wayzata, Minn.

[73] Assignee: SciMed Life Systems, Inc., Maple Grove, Minn.

[21] Appl. No.: 08/951,647

[22] Filed: Oct. 16, 1997

[51] Int. Cl.[7] .................................................. A61B 5/00
[52] U.S. Cl. ............................................................ 600/585
[58] Field of Search ................................ 600/435–436, 600/585

[56] References Cited

U.S. PATENT DOCUMENTS

| | | | |
|---|---|---|---|
| 4,779,628 | 10/1988 | Machok | 600/585 |
| 4,827,941 | 5/1989 | Taylor et al. | 128/657 |
| 4,846,193 | 7/1989 | Tremulis et al. | 128/772 |
| 4,875,489 | 10/1989 | Messner et al. | 128/772 |
| 4,907,332 | 3/1990 | Christain et al. | 29/237 |
| 4,917,103 | 4/1990 | Gambale et al. | 128/772 |
| 4,922,923 | 5/1990 | Gambale et al. | 128/772 |
| 4,966,163 | 10/1990 | Kraus et al. | 128/772 |
| 5,060,660 | 10/1991 | Gambale et al. | 128/772 |
| 5,109,867 | 5/1992 | Twyford, Jr. | 128/772 |
| 5,113,872 | 5/1992 | Jahrmarkt et al. | 128/772 |
| 5,117,838 | 6/1992 | Palmer et al. | 128/772 |
| 5,133,364 | 7/1992 | Palermo et al. | 128/772 |
| 5,139,032 | 8/1992 | Jahrmarkt et al. | 128/772 |
| 5,188,621 | 2/1993 | Samson | 604/283 |
| 5,191,888 | 3/1993 | Palmer et al. | 128/657 |
| 5,195,535 | 3/1993 | Shank | 128/772 |
| 5,197,486 | 3/1993 | Frassica | 128/772 |
| 5,267,573 | 12/1993 | Evans et al. | 128/772 |
| 5,271,415 | 12/1993 | Foerster et al. | 128/772 |
| 5,275,173 | 1/1994 | Samson et al. | 128/772 |
| 5,282,478 | 2/1994 | Fleischhaker, Jr. et al. | 128/772 |
| 5,295,492 | 3/1994 | Sellers | 128/772 |
| 5,361,777 | 11/1994 | Sellers | 128/772 |
| 5,365,944 | 11/1994 | Gambale | 128/772 |
| 5,415,178 | 5/1995 | Hsi et al. | 128/772 |
| 5,421,348 | 6/1995 | Larnard | 128/772 |
| 5,441,055 | 8/1995 | Ales et al. | 128/772 |
| 5,513,650 | 5/1996 | Johansen | 128/772 |
| 5,546,958 | 8/1996 | Thorud et al. | 128/772 |

*Primary Examiner*—Max Hindenburg
*Attorney, Agent, or Firm*—Crompton, Seager & Tufte, LLC

[57] ABSTRACT

An extendable, guide wire providing an apparatus for effecting exchange of over-the-wire catheters without requiring either a double length guide wire or the addition of an extension guide wire. The guide wire includes a distal member for insertion into the patient and a proximal member for extension from the patient, the proximal member having at least one wire strand coiled into a shorten, compressed state. If a catheter exchange is required, the proximal member coil is irreversibly lengthened by drawing the coil proximally, significantly extending the length of the proximal member. Catheter withdrawal and advancement can follow the lengthening. A sheath adapted to slide over and strengthen the drawn wires prior to catheter exchange is also provided.

22 Claims, 1 Drawing Sheet

U.S. Patent     Jun. 27, 2000     6,080,117
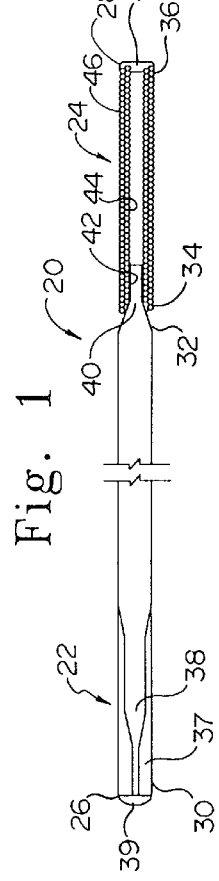
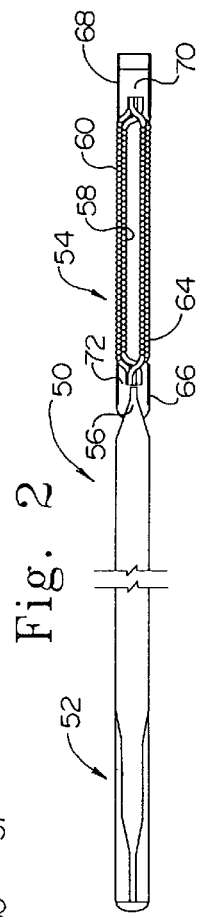
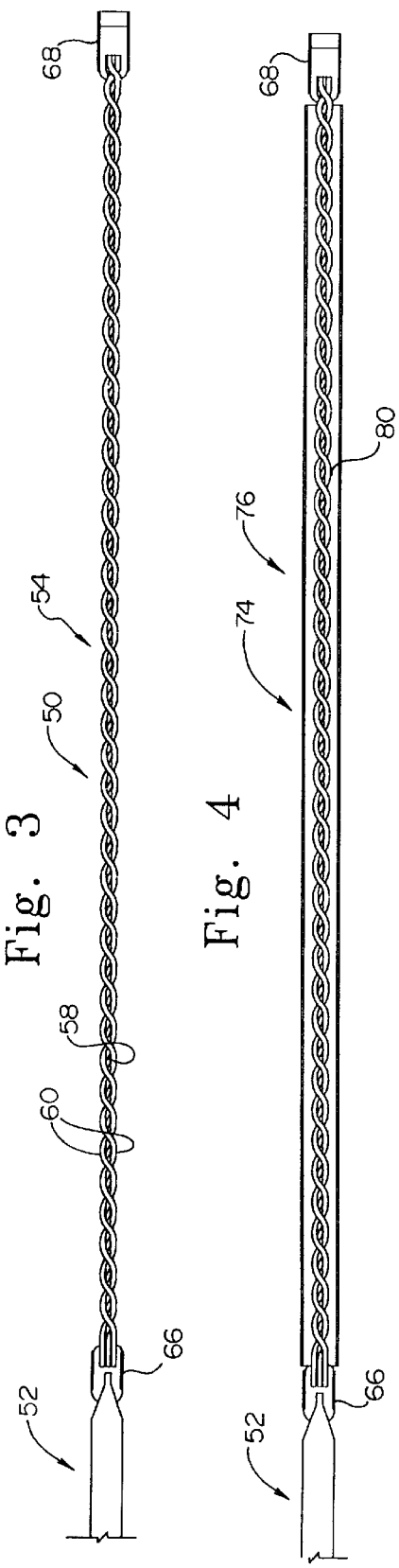
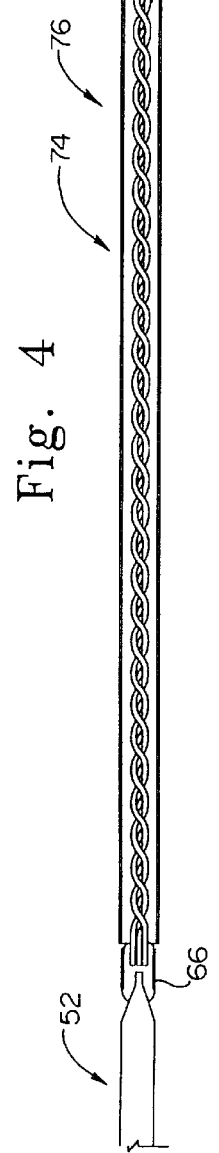
Fig. 1
Fig. 2
Fig. 3
Fig. 4

GUIDE WIRE EXTENSION SYSTEM

FIELD OF THE INVENTION

The present invention relates generally to intravascular guide wires for use in procedures such as angioplasty. More specifically, the present invention relates to an extendable guide wire useful for effecting catheter exchanges.

BACKGROUND OF THE INVENTION

Guide wires are currently used to position catheters within the arterial system for procedures such as angioplasty and angiography. The guide wire is typically advanced within the vasculature of a patient to a desired position, followed by a catheter, advanced over the guide wire. It is often necessary to remove a first catheter from the patient and advance a second catheter into position. When the catheter is in position within the patient, a proximal segment of guide wire extends from the patient. The extending proximal segment can be grasped and used to maintain the position of the guide wire.

Withdrawing a catheter over an in-place guide wire typically requires a guide wire extending from the patient for a length at least as long as the catheter guide wire lumen. This is required so as to present an uncovered portion of the guide wire to grasp. "Over-the-wire" catheters have a guide wire lumen over substantially the entire catheter length. "Single-operator-exchange" catheters can have a shorter guide wire lumen, extending only through the catheter distal region. Withdrawing an over-the-wire catheter over the guide wire would completely cover a standard length guide wire, presenting a problem. This problem has been dealt with in several ways.

The original guide wire can be withdrawn and replaced by a double length, exchange guide wire, providing a graspable guide wire portion during the exchange. This can complicate the procedure as the in-place guide wire must be removed and another inserted. Alternatively, a double length guide wire can be used from the start. This can be awkward as the portion of the guide wire extending from the patients body can be unwieldy, and may be unnecessary, if only the first catheter is needed.

In another method, an extension guide wire is provided and crimped or otherwise joined to the in-place guide wire, thereby creating a double length guide wire for effecting a catheter exchange. The crimping adds an additional step and requires the joining of two extremely small wires in the operating room. Crimping also raises the possibility of wire separation during catheter exchange. What remains to be provided is a guide wire that is not a double length guide wire, yet does not require the joining of an extension guide wire to effect an over-the-wire catheter exchange.

SUMMARY OF THE INVENTION

The present invention includes an extendable guide wire for performing catheter exchanges. The extendable guide wire makes possible over-the-wire catheter exchanges without requiring either a double long guide wire for the entire procedure or the coupling of an extension wire to the guide wire. The guide wire of the present invention includes a distal member and a proximal member, the proximal member distal end being coupled to the proximal end of the distal member. A substantial portion of the distal member extends into the patient.

The proximal member has a first, compressed or shortened state and a second, extended or lengthened state. The proximal member extended length is substantially longer than the proximal member shortened length. One guide wire in accordance with the present invention includes wire strands wound into a coil in the proximal member. The wire strands can be pulled proximally, drawing out the coiled strands into substantially straighter and longer strands. The proximal member can have one coil counter-wound within another coil, which can increase the number of strands present in the lengthened, proximal member. In one embodiment, the strands in the proximal member are braided about one another.

One proximal member includes two, 0.0035 inch diameter wires forming an outer coil, counter-wound over an inner coil formed of two, 0.0025 inch diameter wires. Another proximal member includes two, 0.003 inch diameter wires forming an outer coil, counter-wound over an inner coil formed of a single, 0.0025 inch diameter wire. In one proximal member, the proximal member distal wire ends are secured to the distal member proximal end, and the wire free proximal ends to each other, utilizing brazing. Another proximal member secures the proximal member distal wire ends to the distal member proximal end, and the proximal wire free ends to each other, by inserting the wires within hypotubes and affixing the wires with solder. In one embodiment, a sheath is provided to slide over the proximal member wires after extension, providing a stronger member to advance and retract catheters over.

In use, the guide wire, with proximal member in a shortened, coiled state, is advanced into the patient, leaving the proximal member substantially outside of the body. A first catheter can be advanced over the guide wire distal member. When removal of the first catheter is desired, the proximal guide wire member can be grasped at the proximal end and pulled proximally, thereby elongating the proximal member by drawing out the proximal coil members to a length substantially greater than the compressed shorter length. The proximal member, after lengthening, includes one or more wires which can retain some of three dimensional coil structure and can be intertwined, providing support for sliding catheters thereover. With the proximal member lengthened, the first catheter can be withdrawn proximally over the distal and proximal members, and a second catheter advanced distally over both proximal and distal members.

In one catheter exchange method, a sheath is provided and advanced distally to substantially cover the lengthened proximal wires prior to sliding any catheters thereover. The sheath provides added strength to support the advancement and withdrawal of catheters over the lengthened proximal wires. The strengthening sheath allows use of smaller diameter wires or a smaller number of wires, which can allow for a smaller, compressed proximal member outside diameter and/or compressed length than possible without the sheath.

BRIEF DESCRIPTION OF THE DRAWINGS

FIG. 1 is a fragmentary, side cross-sectional view of a guide wire according to the present invention having two outer strands counter-wound over two inner strands;

FIG. 2 is a fragmentary, side cross-sectional view of a guide wire according to the present invention having two outer strands counter-wound over a single inner strand, with hypotube at either end, shown in a compressed, shortened state;

FIG. 3 is a fragmentary, side cross-sectional view of the guide wire of FIG. 3, shown in an extended, lengthened state; and FIG. 4 is a fragmentary, side cross-sectional view of a guide wire and strengthening extension sheath according to the present invention.

DETAILED DESCRIPTION OF THE PREFERRED EMBODIMENTS

FIG. 1 illustrates a guide wire 20 having a distal member 22, a proximal member 24, a distal end 26 and a proximal end 28. Distal member 22 includes a distal region 30 and a proximal region 32, where distal region 30 includes a distal tapering core portion 38 and a proximal shoulder portion 40. In one embodiment, proximal shoulder portion 40 is about 2 to 4 centimeters in length. Tapering core portion 38 can include a series of conical tapers and straight sections as illustrated in FIG. 1, imparting increased flexibility to distal member distal region 30. Guide wire distal member 22 can be similar in some respects to guide wires disclosed in U.S. Pat. No. 5,452,726, entitled INTRAVASCULAR GUIDE WIRE AND METHOD OF MANUFACTURE THEREOF, herein incorporated by reference. A preferred guide wire includes a polymeric distal jacket 37 and a distal tip 39.

In a preferred embodiment, the length of distal guide wire member 22 is about 180 centimeters long. Proximal guide wire member 24 includes a distal region 34, a proximal region 36, and is fixedly attached to distal member 22 as indicated at 42. Proximal member 24 is preferably secured to distal member 22 utilizing brazing. In one embodiment, proximal member 24 is about 35 to 40 centimeters in length in the shortened, compressed state shown in FIG. 1.

Proximal member 24 includes an inner coil 44 and an outer coil 46. As illustrated in FIG. 1, proximal member 24 includes means for length extension within the proximal member itself. In the embodiment illustrated, inner coil 44 includes two, 0.0025 inch diameter wire strands, wound clockwise with a pitch of about 0.0050 inches, and having a coil inside diameter of about 0.003 inches. The pitch is the center to center wire strand spacing. Outer coil 46 includes two, 0.0035 inch diameter wires wound counter-clockwise, with a pitch of about 0.0080, over inner coil 44. Inner coil 44 and outer coil 46 can be attached to each other with brazing, indicated at 48. In a preferred embodiment, coils 44 and 46 are formed of tempered 304 stainless steel wire. While the strands are preferably formed of a metal such as tempered stainless steel, the strands can also be formed of a suitable polymeric material.

In one embodiment, both inner coil 44 and outer coil 46 have the two strands in a side-by-side orientation in the coil. In a preferred embodiment, proximal member 24 can be extended to a length about 250 or 300% longer than the length of the member in the compressed state. When in the extended state, the wires in proximal member 24 stay sufficiently tightly bunched to provide enough column strength to support catheter exchanges. In one embodiment, wires having a circular cross-sectional profile are used to form coils 44 and 46. In another embodiment, wire ribbon is used in place of round wire.

Distal guide wire member 22 in one embodiment is about 0.014 inches in outer diameter as is proximal member 24 in the compressed, shortened state illustrated in FIG. 1. In another embodiment, distal guide wire member 22 has an outside diameter of about 0.018 inch. Having substantially the same outer diameters for both distal and proximal members allows for sliding catheters having guide wire lumens which are closely matched to the distal member to be slid proximally over the proximal member proximal end. In this way, single-operator-exchange catheters, which do not require the proximal member to be extended, may be slipped proximally over the compressed proximal member. While single operator exchange devices may not require use of the extendable proximal member of the present invention, the present invention, properly sized, is compatible with the use of single operator exchange devices.

Referring now to FIG. 2, another guide wire embodiment 50 is illustrated, having a distal member 52 and a proximal member 54. Distal member 52 is similar to distal member 22 of FIG. 1, but has a stepped, tapered shoulder 56 rather than the continuously tapering shoulder 40 of FIG. 1. Proximal member 54 includes an inner coil 58 and an outer coil 60. Inner coil 58 is formed of a single 0.0025 inch diameter wire wound clockwise to have a 0.003 inch inside diameter center and having a pitch of about 0.0028 inch. Outer coil 60 is formed of two, 0.003 inch diameter wires wound counter-clockwise about inner coil 58 and having a pitch of about 0.006 inch. Both wires are preferably formed of 304 stainless steel.

Distal member 52 is joined to proximal member 54 at a distal hypotube junction 66, having a portion of distal member shoulder 62 and proximal member 54 within, secured with solder as indicated at 72. Distal hypotube section 64 is about 1 centimeter long and has an outside diameter of about 0.015 inch and an inside diameter of about 0.011 inch in a preferred embodiment. A proximal hypotube junction 68 binds the proximal ends of inner coil 58 and outer coil 60. Hypotube 68 is secured to coils 58 and 60 with solder, as indicated at 70. Hyptotube section 68 is about 2 centimeters long and has an outside diameter of about 0.011 inches and an inside diameter of about 0.007 inch in a preferred embodiment. In a preferred embodiment, proximal member 54 is about 25 centimeters in length. Proximal member 54 has about a 0.014 inch outside diameter in the compressed state, approximately the same outside diameter as distal guide wire member 52.

Referring now to FIG. 3, guide wire 50 is illustrated in an extended state. Inner coil 58 and outer coil 60 are extended to a length of about 120 centimeters in one embodiment. Extending proximal member 54 to this length also decreases the outside diameter of outer coil 60 from about 0.014 to 0.009 inches. Proximal member 54 can be extended by holding hypotube 66 while pulling hypotube 60 proximally. In the extended state, wires comprising coils 58 and 60 are substantially plastically rather than elastically deformed. It is preferable that the wires in the extended state exhibit little tendency to return to the compressed, coiled configuration. In the extended state, the wires do retain some of the three-dimensional coil structure from the compressed, tightly coiled state. In the extended state, the wires also are intertwined or braided with one another. The retention of three dimensional structure and intertwining provides added structural support and strength relative to three wires simply running in parallel. The intertwined wires have sufficient column strength to support the withdrawal and advancement of catheters over the wires.

Referring now to FIG. 4, another embodiment guide wire 74 is illustrated, having a distal member 52 and a proximal member 76. Proximal member 76 shares some features with proximal member 54 of FIG. 3, but can be formed of smaller diameter proximal member wires 80. This may be preferable when use of a smaller diameter proximal member is desired, as may be the case when a small diameter distal member is used. After extending proximal member 76 to the length shown in FIG. 4, a sheath or tube 78 can be slid over wires 80 as illustrated in FIG. 4. In this way, wires 80 can serve as pilot wires for sheath 78. In a preferred embodiment, sheath 78 is a 3 layer tube, having a polyimide tube with an inner and an outer Teflon® lining. In a preferred embodiment, sheath 78 is about 0.014 inches in outside diameter and has an inner diameter of about 0.012. Sheath 78 can serve to provide increased column strength for wires 80 when advancing and retracting catheters over proximal member 76. The Teflon® inner layer increases the ease of sliding sheath 80 over wires 80, while the Teflon® outer layer allows catheters to be more easily slid over the outside of sheath 80, decreasing the required strength for wires 80.

Numerous characteristics and advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The inventions's scope is, of course, defined in the language in which the appended claims are expressed.

What is claimed is:

1. An extendable guide wire having a distal end and a proximal end comprising:
   a first, elongate, distal member having a distal region and a proximal region;
   a second, elongate, proximal member having a distal region, a proximal region and a length, said proximal member distal region attached to said distal member proximal region, said proximal member including means for increasing said proximal member length, wherein said proximal member length is increased by plastically deforming said proximal member in tension.

2. An extendable guide wire as recited in claim 1, wherein said proximal member length increasing means is contained within said proximal member.

3. An extendable guide wire as recited in claim 2, wherein said proximal member includes an elongate strand, wherein said length increasing means includes said strand being coiled, such that said length can be increased by pulling said strand proximally.

4. An extendable guide wire as recited in claim 3, wherein said strand is formed of a metallic wire.

5. An extendable guide wire as recited in claim 2, wherein said proximal member includes at least two elongate strands, wherein said length increasing means includes said strands being coiled, such that said length can be increased by pulling said strands proximally.

6. An extendable guide wire as recited in claim 5, wherein said strands are formed of metallic wire.

7. An extendable guide wire as recited in claim 5, wherein at least one of said strands is coiled within another of said strand coils.

8. An extendable guide wire as recited in claim 5, wherein said proximal member includes at least two strands wound in an outer helix about at least one inner strand wound in a coil within said outer helix.

9. An extendable guide wire as recited in claim 2, wherein said proximal member includes at least three wire strands, wherein said length increasing means includes said strands being coiled and braided about one another, such that said length can be increased by pulling said strands proximally.

10. An extendable guide wire having a distal end and a proximal end comprising:
    a first, elongate, distal member having a distal region and a proximal region;
    a second, elongate, proximal member having a distal region, a proximal region, an unextended length, and an extended length, said extended length being greater than said compressed length by greater than about 250% of said unextended length, said proximal member distal region attached to said distal member proximal region, and said proximal member including means for containing at least one elongate strand.

11. An extendable guide wire as recited in claim 10, further comprising an elongate, tubular sheath adapted to slidably receive said guide wire proximal member in said second, extended state.

12. An extendable guide wire having a distal end and a proximal end comprising:
    a first, elongate, distal member having a distal region and a proximal region;
    a second, elongate, proximal member having a distal region, a proximal region and a length, said proximal member distal region attached to said distal member proximal region, said proximal member including at least one elongate strand having a first, compressed state having a compressed length, and a second, extended, state having a substantially longer length than said compressed state length.

13. An extendable guide wire as recited in claim 12, wherein said strand forms a coil in said first, compressed state.

14. An extendable guide wire as recited in claim 13, wherein said strand is a wire.

15. A method for exchanging a catheter comprising:
    providing an extendable guide wire having a distal end and a proximal end including
      a first, elongate, distal member having a distal region and a proximal region,
      a second, elongate, proximal member having a distal region, a proximal region and a length, said proximal member distal region attached to said distal member proximal region, said proximal member including means for increasing said length, wherein said length increasing means is contained within said proximal member,
      said proximal member having a first, compressed state having a first length and a second, extended state having a second length greater than said first length;
    positioning said guide wire distally within a patient, wherein said guide wire proximal member is in said compressed state and is extending from said patient;
    sliding a first catheter having a proximal end distally over said positioned guide wire such that said proximal guide wire member proximal region extends proximally past said first cat het e r proximal end;
    pulling said guide wire proximal member proximally such that said proximal member attains said second, extended state;
    withdrawing said first catheter proximally over said guide wire extended proximal member; and
    advancing a second catheter distally over said guide wire proximal and distal members.

16. A method for exchanging catheters as recited in claim 15, wherein said proximal member includes an elongate strand, said strand being coiled, wherein said length increasing means includes extending said proximal portion strand length by pulling said strand proximally.

17. A method for exchanging catheters as recited in claim 16, wherein said proximal member includes at least two elongate strands, said strands being coiled, wherein said length increasing means includes extending said proximal portion strand lengths by pulling said strands proximally.

18. A method for exchanging catheters as recited in claim 17, wherein at least one of said strand coils lies within another of said strand coils.

19. A method for exchanging catheters as recited in claim 18, wherein said strands are formed of metallic wire.

20. A method for exchanging catheters as recited in claim 15, further comprising:
    providing an elongate sheath having a lumen therethrough adapted to slidably receive said proximal member in said extended state; and
    advancing said sheath over said extended proximal member.

21. A method for exchanging catheters as recited in claim 20, wherein said sheath advancing step occurs prior to said second catheter advancing step.

22. A method for exchanging catheters as recited in claim 20, wherein said sheath advancing step occurs prior to said first catheter withdrawing step.

* * * * *